(12) United States Patent
Lea

(10) Patent No.: US 9,182,171 B2
(45) Date of Patent: Nov. 10, 2015

(54) METHOD AND DEVICE TO REMOVE FLUID AND VAPOR

(75) Inventor: Peter Lea, Toronto (CA)

(73) Assignee: SQI Diagnostics Systems, Inc., Toronto (CA)

(*) Notice: Subject to any disclaimer, the term of this patent is extended or adjusted under 35 U.S.C. 154(b) by 506 days.

(21) Appl. No.: 13/121,489

(22) PCT Filed: Sep. 29, 2009

(86) PCT No.: PCT/CA2009/001370
§ 371 (c)(1),
(2), (4) Date: Jun. 2, 2011

(87) PCT Pub. No.: WO2010/034126
PCT Pub. Date: Apr. 1, 2010

(65) Prior Publication Data
US 2011/0232125 A1    Sep. 29, 2011

(30) Foreign Application Priority Data

Sep. 29, 2008   (CA) .................................... 2639837

(51) Int. Cl.
F26B 7/00    (2006.01)
F26B 5/12    (2006.01)
F26B 5/04    (2006.01)
G01N 35/10   (2006.01)

(52) U.S. Cl.
CPC ... F26B 5/12 (2013.01); F26B 5/04 (2013.01); *B01J 2219/00315* (2013.01); *B01J 2219/00414* (2013.01); *B01J 2219/00605* (2013.01); *B01L 2200/025* (2013.01); *B01L 2400/049* (2013.01); *G01N 35/1074* (2013.01)

(58) Field of Classification Search
CPC ..................... B01L 2400/049; B01L 2200/025
USPC ....................................................... 34/92, 437
See application file for complete search history.

(56) References Cited

U.S. PATENT DOCUMENTS 3,650,306 A *  3/1972  Lancaster ..................... 141/238
5,951,783 A    9/1999  Kontorovich et al.
8,030,080 B2 * 10/2011  Spence et al. ................... 436/43

(Continued)

FOREIGN PATENT DOCUMENTS

CA    2574839 A1   3/2006
EP    0123786      7/1984

(Continued)

OTHER PUBLICATIONS

International Search Report dated Jan. 4, 2010.

(Continued)

*Primary Examiner* — Kenneth Rinehart
*Assistant Examiner* — Gajanan M Prabhu
(74) *Attorney, Agent, or Firm* — Pepper Hamilton LLP

(57) ABSTRACT

The present invention relates to a method and device for the removal of fluids and vapors in containment, from adjacent surfaces including supporting flat surfaces and substrates, such as protein spots printed in arrays and micro-array formats. This method and device removes fluids and vapors under controlled and repeatable conditions, enabling uniform phases for degree of drying incurred by objects, specimen and structures, including tissues, adsorbed particles and biological substrates, while reducing and preventing impact of meniscus phase surface tension forces.

6 Claims, 3 Drawing Sheets

(56) References Cited

U.S. PATENT DOCUMENTS

| | | |
|---|---|---|
| 2001/0055545 A1 | 12/2001 | Takii et al. |
| 2005/0112783 A1 | 5/2005 | Evans et al. |
| 2006/0051247 A1* | 3/2006 | Micklash et al. ............ 422/100 |
| 2012/0213667 A1* | 8/2012 | Roach et al. .................... 422/63 |

FOREIGN PATENT DOCUMENTS

| | | |
|---|---|---|
| EP | 0 123 786 | 11/1984 |
| JP | S54-001198 | 1/1979 |
| JP | 7-83939 A | 3/1995 |
| JP | H09-311097 | 12/1997 |
| JP | 2008512645 | 4/2008 |
| WO | 2008018904 | 2/2008 |

OTHER PUBLICATIONS

European Patent Office Search Report, dated Feb. 18, 2013.
Chinese Office Action, dated Feb. 17, 2013 (Translated).
Japanese Office Action, dated Jul. 26, 2013 (Translated).
Chinese Office Action dated Aug. 22, 2013 with English translation re: Application Serial No. 200980138233.5; 17pgs.
Corresponding Australian Patent Application No. 2009295324, Office Action dated Jul. 7, 2014.
Australian Patent Examination Report No. 1 dated Jul. 7, 2014.

* cited by examiner

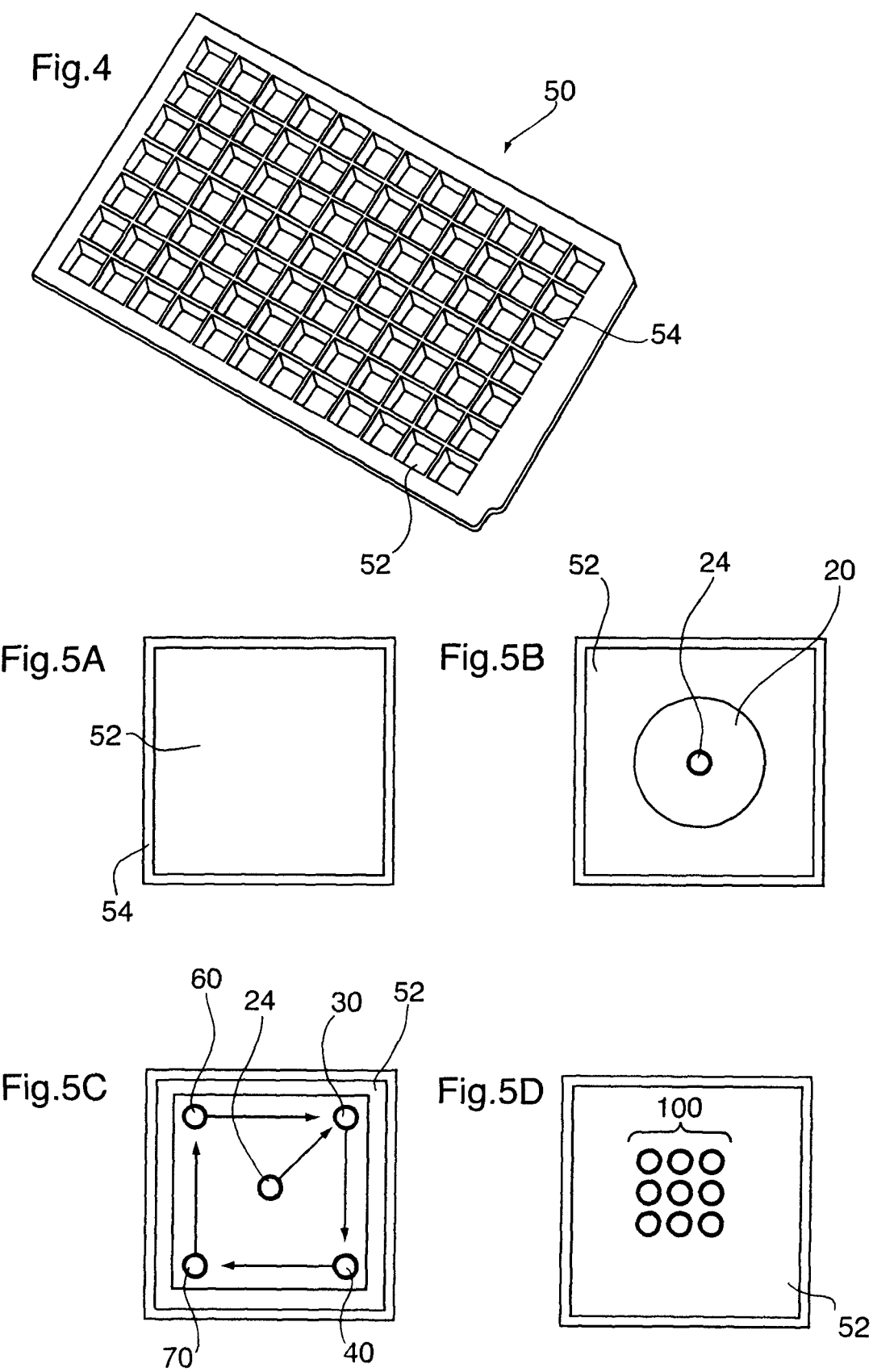

METHOD AND DEVICE TO REMOVE FLUID AND VAPOR

This application is the U.S. National Stage filing under 35 U.S.C. §371 of International Application Ser. No. PCT/CA2009/001370 filed Sep. 29, 2009, which claims priority to Canadian Patent Application Serial No. 2,639,837 filed Sep. 29, 2008, both of which are incorporated herein by reference to their entirety.

FIELD OF THE INVENTION

The present invention relates to a method and device for the removal of fluids and vapors from adjacent assay surfaces including supporting flat surfaces and substrates, such as protein spots printed in arrays and micro-array formats.

DESCRIPTION OF THE RELATED ART

Most soft structures, including biological materials and tissues will collapse, flatten or shrink when subjected to drying. A major defect inherent in uncontrolled air drying involves the passage of the receding air-water interface through the specimen. Throughout the lengthy air drying process, associated surface tension forces exert shear and stress up to approximately 2000 p.s.i (pounds per square inch). To prevent collapse and distortion and destruction of soft structures it is mandatory to modulate passage of the interface over surfaces and or through the structure to be dried. This can be accomplished to the level of nanostructure preservation using complex techniques, including freeze-drying, critical point drying or other complex vacuum drying procedures. These techniques are inherently difficult to implement.

Another problem is positioning drying devices onto carrier substrates within confined spaces, to realize an unobstructed pathway so that any pathogens contained in test fluids, in aerosols and or in the bio-array will be contained within the drying device and be effectively removed and inactivated during the process to prevent cross-contamination and protect personnel from being infected.

A need exists for an improved method and apparatus for removing excess bulk processing fluids followed by controlled and contained removal of fluid vapors in the vicinity of the object or substrate to be dried, to enable enhanced preservation. It is desirable to provide such method of bulk fluid removal followed by vapor removal using apparatus that is effective and is controllable, generally adjustable, light-weight and simple to implement.

There is a further need for a method and device that removes fluids and vapors under controlled and repeatable conditions, enabling uniform phases for degree of drying incurred by objects, specimen and structures, including tissues, adsorbed particles and biological substrates, while reducing and preventing impact of meniscus phase surface tension forces.

SUMMARY OF THE INVENTION

The present invention provides a method for removing fluids and vapors from an assay surface. The method involves two phases. In the first phase, an aspiration tube connected to a vacuum is used to remove bulk fluids from the assay surface. The aspiration tube is displaced relative to the assay surface during this phase as it removes bulk fluid. Once bulk fluid is removed, a second phase is employed in which a vacuum is applied to the aspiration tube for removing residual vapors.

The invention includes an apparatus for carrying out the method. The apparatus includes an aspiration tube connected to a vacuum source for removing vapor and fluid. The aspiration tube is attached to a moveable platform which is displaced by an actuator.

According to one aspect of the present invention, there is provided an apparatus for the removal of fluids and vapors from a surface comprising: a moveable platform connected to a displacement means; an aspiration tube having open first and second ends, the second end of the aspiration tube being connected to the moveable platform; and a vacuum source connected to the second end of the aspiration tube for applying a vacuum through said tube.

According to another aspect of the invention, there is provided a method for drying a surface defining at least one well comprising the following steps: providing a drying apparatus comprising a moveable platform connected to a displacement means, an aspiration tube having open first and second ends, the second end of the aspiration tube being connected to the moveable platform, and a vacuum source connected to the second end of the aspiration tube for applying a vacuum through said tube; placing the first end of the aspiration tube in proximity to a center of said at least one well; applying a vacuum through said aspiration tube for removing bulk fluid from said well; moving the aspiration tube from the center of the well to a peripheral edge of said well and the about the periphery of said well for removing the bulk fluid from said well; removing the aspiration tube from said well; moving said aspiration tube so that the first end of the aspiration tube is a predetermined distance from the well; and applying a vacuum through said aspiration tube for removing vapor from said well.

BRIEF DESCRIPTION OF THE DRAWINGS

FIG. 4 is top elevation view of an assay device that can be dried by the drying apparatus of the present invention; and FIG. 5 is schematic flow chart showing a sequence of actions to be followed for controlled removal of bulk fluid according to the present invention.

DETAILED DESCRIPTION OF THE PREFERRED EMBODIMENTS

Figure 1:
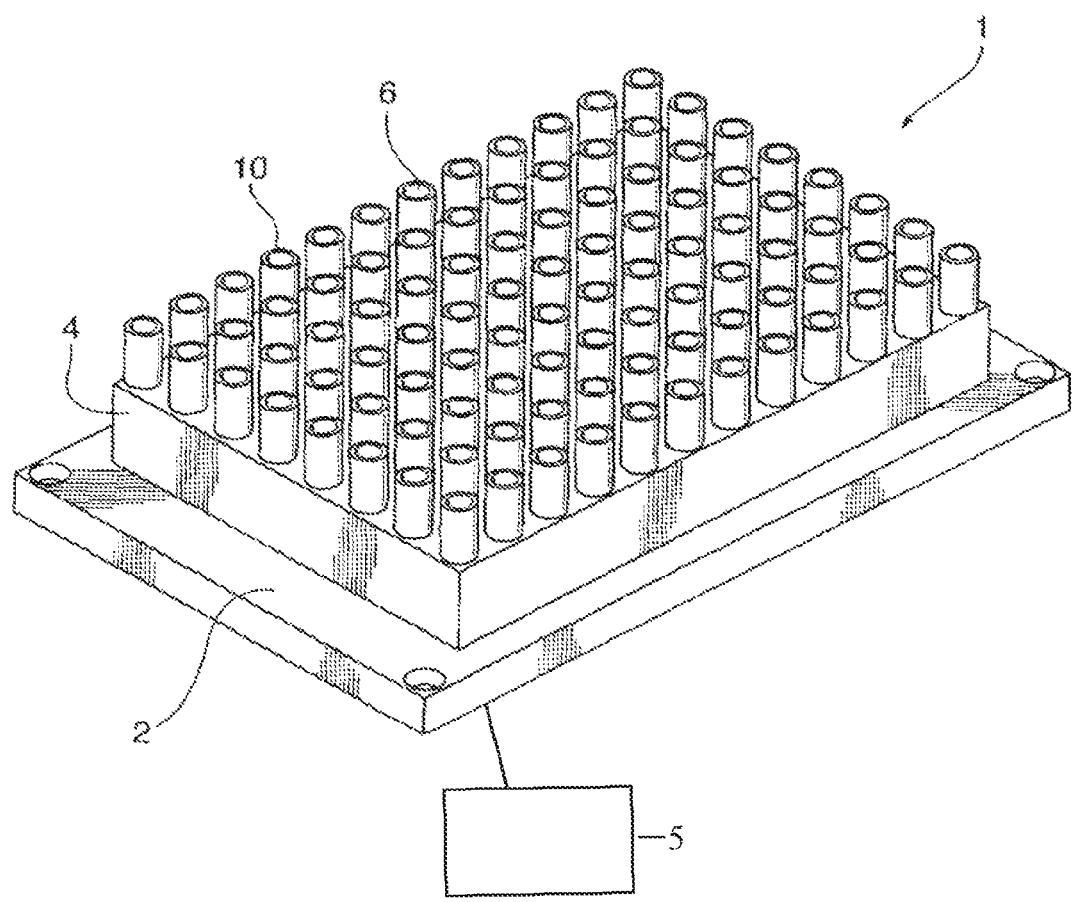
FIG. 1 is a perspective view of a preferred embodiment of a drying apparatus of the present invention.
Figure 2:
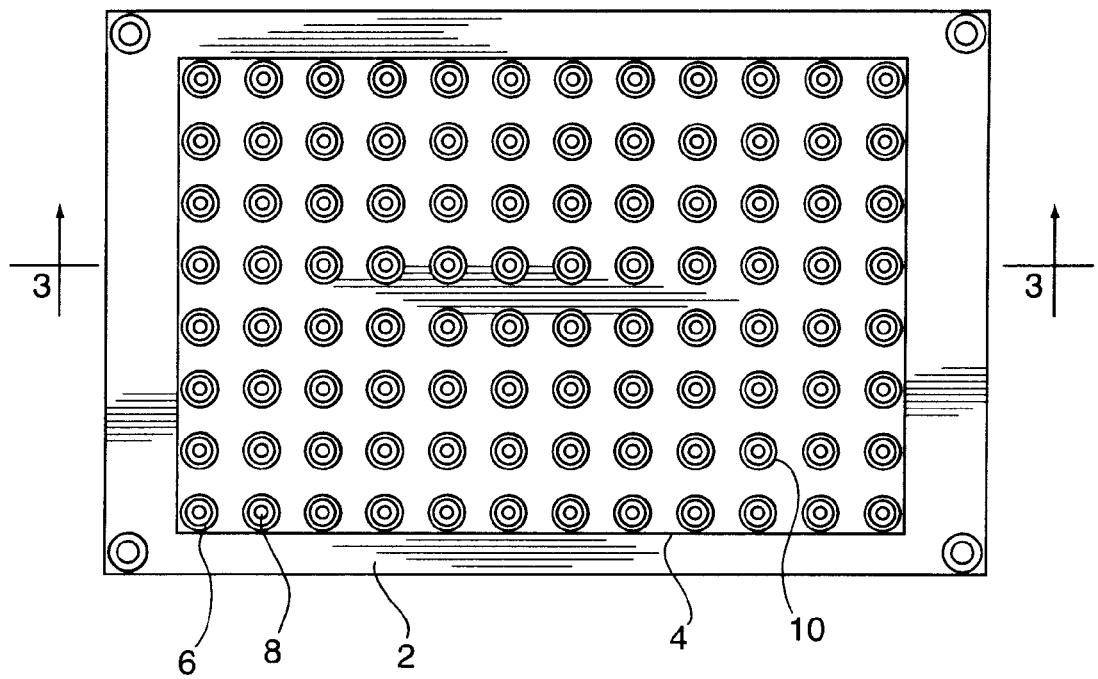
FIG. 2 is a bottom view of the preferred embodiment of a drying apparatus of the present invention.

As shown in FIG. 1, drying apparatus 1 has a frame 2. The frame 2 can be coupled to an actuator 5 that moves the frame in three dimensions along an XYZ plane. The actuator 5 functions as a displacement means and can be one of many actuators known in the art. A preferred actuator is ELx405 Microplate Washer, BioTek Instruments, U.S.A.
to an actuator (not shown) that moves the frame in three dimensions along an XYZ plane. The actuator functions as a displacement means and can be one of many actuators known in the art. A preferred actuator is ELx405 Microplate Washer, BioTek Instruments, U.S.A.

Figure 3:
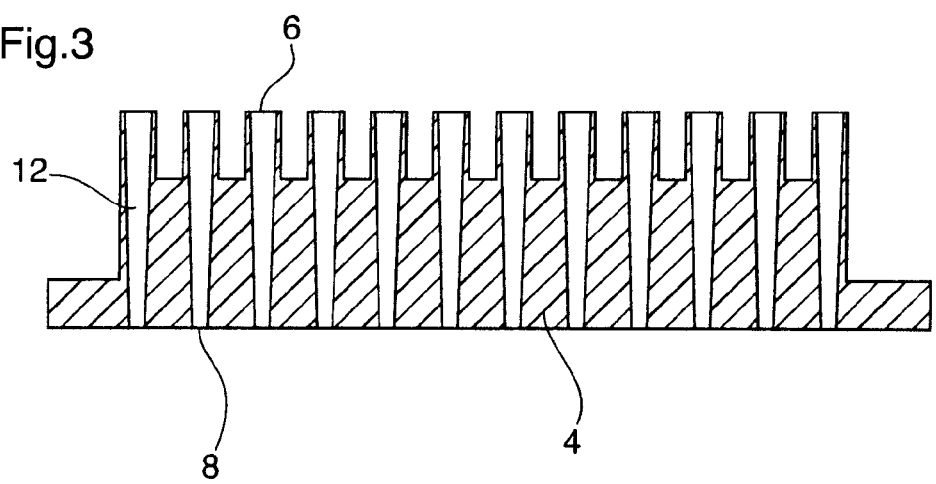
FIG. 3 is a cross-sectional view taken along the line 3-3 of FIG. 2.

The drying apparatus includes a housing 4 that is attached to the frame 2. A plurality of aspiration tubes 10 is located in the housing. In alternate embodiments, the dryer can have as few as one tube. Each of the tubes 10 defines a length, and defines a longitudinal bore 12 along the length between a first open end 6 and a second open end 8. As shown in FIG. 3, the longitudinal bore 12 is preferably tapered wherein the first open end 6 has a greater diameter than the diameter of the second open end 8.

The length of the aspiration tube 10 may vary. In the preferred embodiment, the length is sufficient to maintain an aspect ratio of about 18 derived in concert with opening diameters aspect ratio of about 1.7 based on cone angle pitch at 3.5 degrees. The wall thickness of the aspiration tube 10 at the first open end 6 in proximity of a substrate is preferably about 400 µm. The diameter of the first open end 6 is about 5 mm. The second open end 6 has a diameter of about 2 mm, a preferred diameter to allow constant airflow through all aspiration tubes 10 into a vacuum head being modulated by setting of the flow access across the substrate surface area as defined by the perimeter and wall height ratio of an assay device containing a removable fluid load.

The drying apparatus 1 includes means for applying a vacuum to the second open end 8 of each aspiration tube. The means for applying a vacuum can be any of various such means known in the art. In the preferred embodiment, the vacuum means is Vacuum pump, ME 4C NT Vario, VacuuBrand, U.S.A.

The dryer apparatus 1 of the preferred embodiment is preferably used to dry an assay device and in particular of the type such as assay device 50 shown in FIG. 4. The assay device 50 has a plurality of wells 52. Each of said wells 50 are separated by intersecting walls 54; providing effectively a superstructure onto the plate, thereby forming a single well or separate multiple wells. Multiple wells have the added benefit of allowing multiple objects to be processed on the same plate as each well can have an assay printed thereon in form of protein spots micro-array format, for example.

In operation, the present invention provides a two step method for removal of fluids and vapors, especially from micro-array protein spot assay devices. The method implemented by the dryer apparatus 1 involves first removing relatively larger quantities of bulk fluids from the surface of an assay device typically used in washing and processing protein spot micro-arrays, followed by removal of remaining fluid vapors to effectively induce uniform states of hydration in the three dimensional protein spots that constitute a micro-array. Without being bound by theory, it has been found that the micro-array constituent state of hydration directly affects the signal intensity thereby enabling enhanced quantitative analysis of bio-array data, especially when applied to diagnostic grade micro-array signals. The method of the present invention provides drying of protein spot bio-array formats without inducing negative and disruptive effects, ensuring that, as fluids and vapors are removed directly or with induced air flow over the protein spot bio-array surfaces; these removed media simultaneously are contained and decontaminated to prevent dissipation of infectious materials into the environment.

Phase 1 of the drying method involves the removal of bulk fluid from the wells of the assay device. For removing the bulk fluid, the platform is moved to sequentially displace the aspiration tubes relative to their corresponding wells in a specific and pre-determined displacement pattern in order to provide uniform drying. In phase 1, fluid removal is initiated when immersing an aspiration tube 10, into the centre of a well 52 or volume of fluid to be removed from a surface, to a pre-determined height above a supporting substrate. An aspiration vacuum is applied through the aspiration tube 10 to generate sufficient air pressure by suction to effect sequential displacement of fluid, as illustrated in FIG. 5B. The fluid contained in well 52 is removed to leave a semi-dry area of the substrate, such as well 52. The remaining bulk fluid, around the periphery of the well 52, is bound in situ by meniscus forces and the retaining walls 54. This remaining bulk fluid is immediately aspirated via the aspiration tube 10 as the aspiration tube traces a preferred and controlled aspiration path as shown by the arrows in FIG. 5C. Preferably, the displacement means moves the aspiration tube 10 from a centre position 24 to a first peripheral position 30 then to a second peripheral position 40 then to a third peripheral position 70 and then to a fourth peripheral position 60 to complete a peripheral fluid removal course at position 30. In the preferred embodiment, the wells are square shaped; and the first, second, third and fourth peripheral positions are corners of the square. A person skilled in the art will understand that the method can be implemented on wells of any shape by moving the aspiration tube 10 along positions around the periphery of the given shape of the well.

The height spacing of the aspiration tube 10, i.e. the distance above the substrate, preferably ranges from 50 µm to 2 mm, with a most preferred setting of 200 µm. FIG. 5D illustrates a well 52 with fluid removed, showing a now partially dried object—which in the preferred embodiment is a dried protein spot micro-array 100—as remaining in a well 52. The protein spot micro-array may be on another substrate in alternate embodiments. In alternate embodiments, objects other than a protein spot micro-array located in a well or on a substrate may also be dried according to the present method. Without being bound by theory, we believe that the present invention avoids disruptive energy dissipation being released on the object as sequential fluid meniscus phases are passing through and around the object and over substrates.

When the phase 1 rapid, non-destructive displacement of bulk fluid is complete, partially dry objects and wells 52 or other substrates continue to contain and be enveloped by fluid vapors. Phase 2, vapor phase removal is immediately activated and accomplished by modulating air flow over the vapor logged, differentially hydrated substrate platform and partially dry object. Effectively, dryer apparatus 1 modulated air flow currents under controlled conditions are actively moved across vapor sources to remove vapors, resulting in a consistent state of dehydration of objects located within the vacuum induced air flow currents. The induced air flow currents simultaneously contain, isolate and disinfect the possibly contaminated and/or infectious materials carried within the consequent moist exhaust air flow.

Phase 2 vapor removal is applied by drying apparatus 1 in order to equilibrate any fluid vapor still remaining about and within a well 52 upon completion of phase 1 fluid removal. The preferred vacuum applied to air flow modulation ranges between about 106 decaPascals to about 10132 decaPascals. The X-Y co-ordinate matrix spacing of the tubes 10, in the preferred embodiment, coincides with the X-Y co-ordinate matrix placement of the well superstructure attached to the assay device 50. As both X-Y matrices provide accurate alignment, each well 52 will have a single aspiration tube 10 inserted at the centre of each well 52, with the aspiration tube 10 first opening 6 placed at a predetermined, optimal distance above the surface of the plate substrate which preferably ranges from about 10 µm to 7 mm. The preferred setting provides optimal air flow when the height of the intake end of the aspiration tube is set about 2 mm above a protein spot micro-array, and the space from the perimeter of the aspiration tube 10, at the intake opening, to the nearest well wall 54 measures about 1 mm. Vacuum aspiration removes any residual fluid vapor.

While the present invention has been described with reference to embodiments details of the invention shown in the drawings, these embodiments are not intended to limit the scope of the invention as claimed in the appended claims.

What is claimed is:

1. A method for drying a surface defining at least one well comprising the following steps:
    providing a drying apparatus comprising a moveable platform coupled to an actuator configured to displace the movable platform, an aspiration tube having open first and second ends, the second end of the aspiration tube being connected to the moveable platform, and a vacuum source connected to the second end of the aspiration tube for applying a vacuum through said tube, said aspiration vibe defining a length and defining a longitudinal bore along said length;
    placing the first end of the aspiration tube in proximity to a center of said at least one well;
    removing bulk fluid from said at least one well by:
        applying a first vacuum through said aspiration tube; and
        moving the aspiration tube along an XYZ plane from the center of said at least one well to a peripheral edge of said at least one well and about the periphery of said at least one well;
    removing the aspiration tube from said at least one well;
    moving said aspiration tube so that the first end of the aspiration tube is a predetermined distance above said at least one well; and
    removing vapor from said at least one well by applying a second vacuum through said aspiration tube;
    wherein said bore has a tapered diameter such that said first end has a larger diameter than said second end.

2. The method of claim 1 comprising a plurality of tubes, the at least one well comprising a plurality of wells, each of said tubes being adapted to interact with one of said wells.

3. The method of claim 1 wherein the predetermined distance is from 50 μm to 2 mm.

4. The method of claim 1 wherein said length is sufficient to maintain an aspect ratio of about 18 derived in concert with opening diameters aspect ratio of about 1.7 based on cone angle pitch at 3.5 degrees.

5. The method of claim 1 wherein said aspiration tube has a thickness of about 400 μm at said first end.

6. The method of claim 1 wherein the diameter of the aspiration tube at said second end is about 2 mm.

* * * * *